(12) United States Patent
Kuriger et al.

(10) Patent No.: US 8,398,567 B2
(45) Date of Patent: Mar. 19, 2013

(54) METHOD AND APPARATUS FOR MEASURING AN ANALYTE IN A BODY FLUID

(75) Inventors: Rex J. Kuriger, Granger, IN (US); Andrew J. Dosmann, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 712 days.

(21) Appl. No.: 10/590,531

(22) PCT Filed: Feb. 4, 2005

(86) PCT No.: PCT/US2005/003621
§ 371 (c)(1),
(2), (4) Date: Aug. 24, 2006

(87) PCT Pub. No.: WO2005/077274
PCT Pub. Date: Aug. 25, 2005

(65) Prior Publication Data
US 2007/0213636 A1 Sep. 13, 2007

Related U.S. Application Data

(60) Provisional application No. 60/542,363, filed on Feb. 6, 2004.

(51) Int. Cl.
*A61B 5/00* (2006.01)
*A61B 17/14* (2006.01)
*A61B 17/32* (2006.01)

(52) U.S. Cl. .......................... 600/583; 606/181; 606/182

(58) Field of Classification Search .................. 600/573, 600/576, 578, 583, 584; 604/164.01; 606/181
See application file for complete search history.

(56) References Cited

U.S. PATENT DOCUMENTS

| | | | | |
|---|---|---|---|---|
| 2,830,587 A | | 4/1958 | Everett | 128/221 |
| 4,627,445 A | * | 12/1986 | Garcia et al. | 600/583 |
| 4,637,403 A | | 1/1987 | Garcia et al. | 128/770 |
| 5,029,583 A | | 7/1991 | Meserol et al. | 128/633 |
| 5,278,079 A | | 1/1994 | Gubinski et al. | 436/165 |
| 5,368,047 A | | 11/1994 | Suzuki et al. | 128/765 |
| 5,518,689 A | | 5/1996 | Dosmann et al. | 422/82.05 |
| 5,540,709 A | | 7/1996 | Ramel | 606/183 |
| 5,611,999 A | | 3/1997 | Dosmann et al. | 422/82.05 |

(Continued)

FOREIGN PATENT DOCUMENTS

| EP | 0 447 726 | 9/1991 |
|---|---|---|
| EP | 1 342 448 | 9/2003 |

(Continued)

OTHER PUBLICATIONS

International Search Report dated May 24, 2005 for International Application No. PCT/US2005/003621 (6 pages).

*Primary Examiner* — Jeffrey G Hoekstra
*Assistant Examiner* — Adam Eiseman
(74) *Attorney, Agent, or Firm* — Nixon Peabody LLP

(57) ABSTRACT

An apparatus and method for analyzing an analyte in a body fluid sample using a lancing device (10) having a hollow lancet are disclosed. According to one embodiment of the present invention, the method comprises the acts of lancing the skin of a test subject with the hollow lancet (18) having an interior of the hollow lancet (18) that forms a capillary channel, collecting a body fluid sample from the lanced skin in the capillary channel of the hollow lancet (18), and analyzing the body fluid sample for determining the analyte concentration in the body fluid sample while the collected body fluid sample remains in the lancet (18).

33 Claims, 3 Drawing Sheets

U.S. PATENT DOCUMENTS

| | | | |
|---|---|---|---|
| 5,801,057 A | 9/1998 | Smart et al. | 436/68 |
| 5,951,492 A * | 9/1999 | Douglas et al. | 600/583 |
| 6,071,249 A | 6/2000 | Cunningham et al. | 600/578 |
| 6,152,942 A | 11/2000 | Brenneman et al. | 606/181 |
| 6,181,417 B1 | 1/2001 | Dosmann | 356/326 |
| 6,214,626 B1 | 4/2001 | Meller et al. | 436/165 |
| 6,652,809 B1 | 11/2003 | Comley et al. | 422/82.05 |
| 6,896,850 B2 * | 5/2005 | Subramanian et al. | 422/102 |
| 6,922,576 B2 | 7/2005 | Raskas | 600/316 |
| 2003/0018282 A1 * | 1/2003 | Effenhauser et al. | 600/583 |
| 2003/0018300 A1 | 1/2003 | Duchon et al. | 604/164.01 |
| 2003/0171696 A1 | 9/2003 | Dosmann | 600/583 |
| 2004/0127818 A1 * | 7/2004 | Roe et al. | 600/583 |

FOREIGN PATENT DOCUMENTS

JP 09108202 4/1997

* cited by examiner

METHOD AND APPARATUS FOR MEASURING AN ANALYTE IN A BODY FLUID

CROSS-REFERENCE To RELATED APPLICATIONS

This application claims priority to application Ser. No. 60/542,363, filed on Feb. 6, 2004, which is incorporated by reference in its entirety.

FIELD OF THE INVENTION

The present invention relates generally to testing systems for determining the concentration of an analyte in a fluid sample, and more particularly, to a system for lancing a test subject's skin, harvesting a body fluid sample, and determining the concentration of an analyte in the body fluid sample.

BACKGROUND OF THE INVENTION

It is often necessary to quickly obtain a sample of blood and perform an analysis of the blood sample. One example of a need for obtaining a sample of blood is in connection with a blood glucose monitoring system, which a user must frequently use to monitor the user's blood glucose level.

One method of obtaining a blood sample and analyzing the sample for determining the glucose level is with a lancing device and a separate blood collection device. In obtaining a blood sample, a drop of blood is obtained from the fingertip using the lancing device, and the blood is harvested using a test strip, which is then analyzed by a test unit to determine the glucose concentration in the blood, often using an electrochemical- or colorimetric-based analysis. Test strips are also used for determining the concentration or presence of various other analytes (e.g., fructosamine, hemoglobin, cholesterol, glucose, alcohol, drugs including illegal drugs, etc.) in a variety of body fluids (e.g., blood, interstitial fluid, saliva, urine, etc.).

A drawback associated with using physically separate lancing and collection devices is that a patient/user must manipulate two different instruments requiring the user/patient to bring the collection device (e.g., the test strip) to the area of skin that has been lanced to collect the sample. Because the user must align the collection device with the sample to be collected, a larger than necessary sample amount is often produced and collected to ensure an accurate analysis. In other situations, not enough sample is collected for accurate analysis because the collection device is not properly positioned. This problem can be further compounded if the user has impaired vision or poor dexterity. Because test systems are requiring smaller volumes of blood for analysis, it becomes more difficult to position a collection instrument for proper collection. Further impacting the self-testing process is that some users are adverse to the pain associated with repeated lancings.

SUMMARY OF THE INVENTION

An apparatus and method for analyzing an analyte in a body fluid sample using a lancing device having a hollow lancet are disclosed. According to one embodiment of the present invention, the method comprises the acts of lancing the skin of a test subject with the hollow lancet having an interior of the hollow lancet that forms a capillary channel, collecting a body fluid sample from the lanced skin in the capillary channel of the hollow lancet, and analyzing the body fluid sample for determining the analyte concentration in the body fluid sample while the collected body fluid sample remains in the lancet.

The above summary of the present invention is not intended to represent each embodiment, or every aspect, of the present invention. Additional features and benefits of the present invention will become apparent from the detailed description, figures, and claims set forth below.

Figure 1:
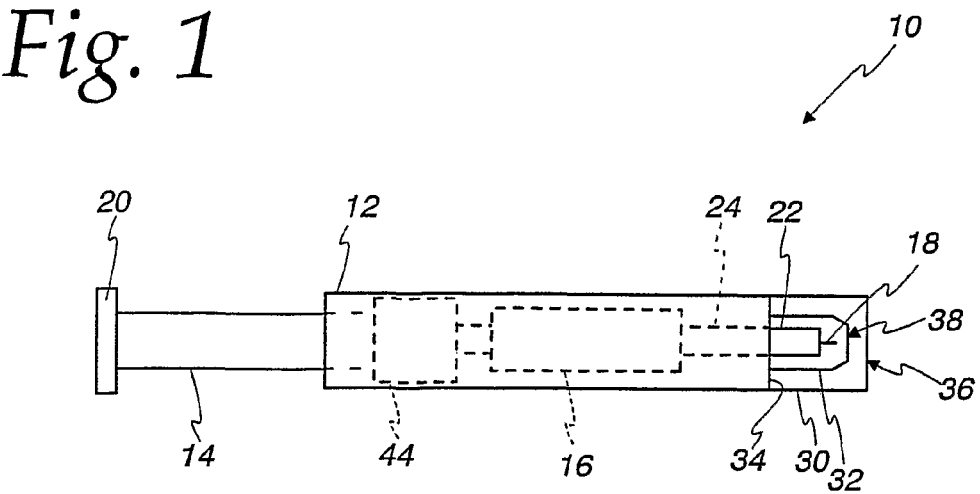
FIG. 1 is a side view of a lancing device according to one embodiment of the present invention.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE ILLUSTRATED EMBODIMENTS

Figure 2:
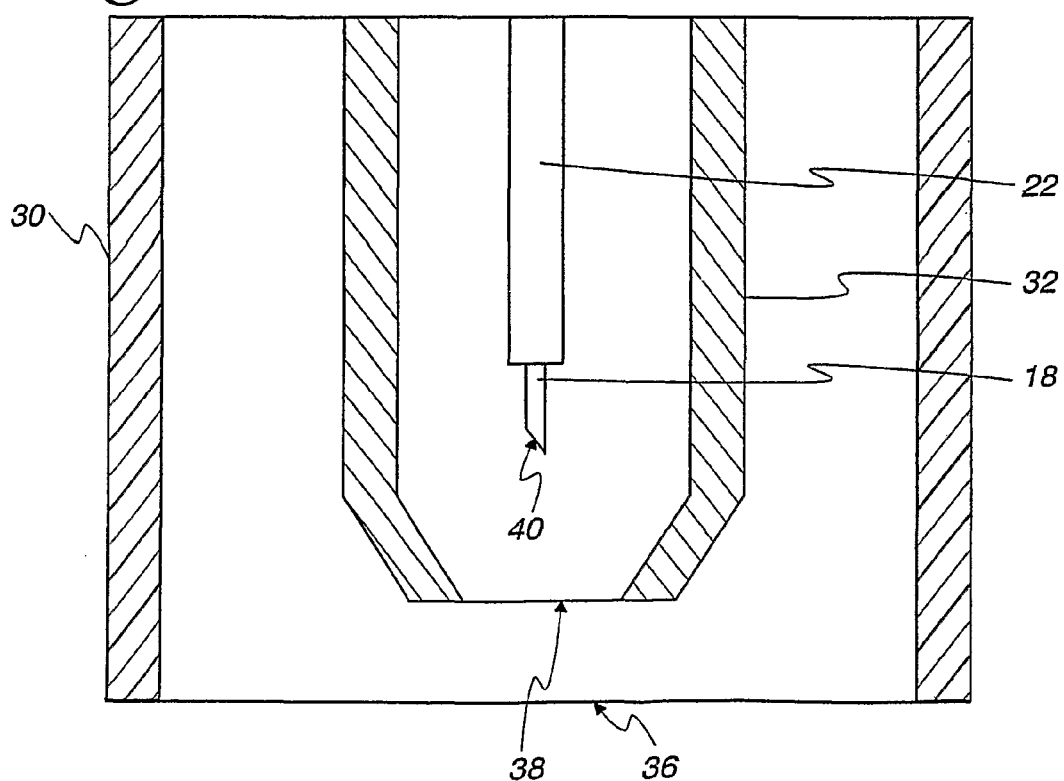
FIG. 2 is an enlarged cross-sectional view of the forward end of the lancing device of FIG. 1.

Turning now to the drawings and initially to FIGS. 1 and 2, a lancing device 10 according to one embodiment of the present invention is shown. In the illustrated embodiment of the present invention, the lancing device 10 is vacuum assisted as is described in detail below and as is known in the art. The device 10 includes a body 12 that houses a plunger 14 and a lancing mechanism 16 for driving a lancet 18. A top end 20 of the plunger 14 extends beyond the body 12. In using the lancet 18 to puncture a test subject's skin, a user grasps the device 10 by the body 12 and depresses the top end 20 of the plunger 14—moving the plunger 14 into the body 12 of the device 10—to downwardly advance the lancet 18 into a test subject's skin. The lancet 18, one end of which is embedded in a base 22, is removably attached to a lancet holder 24, which is coupled to the plunger 14 through the lancing mechanism 16 within the body 12.

An end cap including an outer end cap 30 and an inner-locating end cap 32 are removably attached to a forward end 34 of the device 10 opposite the plunger 14. The inner-locating end cap 32 is located within the outer end cap 30. Generally, as is described below, the outer end cap 30 contacts a test subject's skin, and the test subject's skin is pulled against the inner end cap 32 during the ensuing lancing operation for puncturing the test subject's skin and collecting the sample produced at the lance site. Both the outer end cap 30 and the inner end cap 32 have open ends 36, 38 though which the lancet 18 passes to puncture a test subject's skin during the lancing operation. The end caps are removably attached to the lancing device 10 so that a used lancet can be replaced with a new lancet after a lancing procedure. Further, the end caps, which may come into contact with a sample during testing, may also be disposable in some embodiments of the present invention. According to one embodiment of the present invention the outer and inner end caps 30, 32 are integrally formed such that detaching the outer end cap 30 from the forward end 34 of the device 10 also removes the inner end cap 32.

The lancet 18 is constructed of a substantially optically clear material and includes a micro-capillary channel according to one embodiment of the present invention. The lancet 18 has a hollow interior, which forms the micro-capillary channel. The micro-capillary channel includes a reagent or enzymatic indicator system disposed along its inner walls. In operation, as is described in detail below, the lancet 18 is used to both puncture a test subject's skin and then to harvest the body fluid sample produced at the puncture site. The analyte of interest (e.g., glucose) in the collected body fluid sample (e.g., blood) reacts with the reagent disposed within the lancet 18 to produce a colorimetric reaction indicative of the concentration of the analyte in the sample. This reaction is then measured by an optical readhead such as a light detector. The lancet 18 is used for puncturing the test subject's skin, harvesting a sample produced at the punctured area of the test subject's skin, and for providing an area within the lancet 18 that the harvested sample reacts with the reagent. Finally, an optical transmission measurement is used to read the colorimetric reaction within the capillary channel of the lancet 18, and an analysis of the transmitted light is performed for determining the analyte concentration.

According to one embodiment of the present invention, the lancet 18 is a microcapillary tube constructed of fused silica and has a polygonal cross section (e.g., rectangular, square, hexagonal, etc.) In other embodiments of the present invention, the lancet 18 is constructed of another substantially optically clear material such as, for example, pyrex, quartz, acrylic, polycarbonate, or polyester. The puncturing end or tip 40 of the microcapillary tube lancet 18 is cleaved as shown in FIG. 2 at an acute angle with respect to the longitudinal axis of the lancet 18 to form a sharp point. The sharp-puncturing end 40 of the lancet 18 cleanly punctures the test subject's skin to produce a consistently sized sample on the test subject's skin.

According to one embodiment of the present invention, the lancet 18 has a square cross section having an outer dimension of about 300 microns, which is smaller than a 360 micron diameter of a typical 28-gauge steel lancet, resulting in a small puncture site on a test subject's skin. A smaller laceration is desirable because it translates to less pain for the test subject. The fused silica microcapillary tubing for use in constructing the lancet 18 is commercially available having interior channel widths of about 50, 75, or 100 microns, with corresponding volumes of about 13, 29, and 50 nanoliters ("nl"), respectively, for a lancet 18 having a length of about 5 mm, which can used in alternative embodiments of the present invention. The fused silica microcapillary tubing for use in constructing the lancet 18 according to one embodiment of the present invention is commercially available from Polymicro Technologies, LLC of Phoenix, Ariz.

The flat surfaces of the lancet 18 provide a substantially optically clear window for transmitting light through the sample. As is described below, transmission spectroscopy may be used to analyze the sample. The absorbance of the sample reacted with the analyte in the lancet 18 is used to determine analyte concentration. The transmission of light through fused silica, for example, is spectrally flat from the ultra-violet region (e.g., wavelengths ranging from about 350 nm to about 2000 nm) into the infrared region. The square fused microcapillary lancet 18 reduces the path length error associated with transmission spectroscopy measurements. For example, the path length error is limited to one tolerance inside the square fused silica microcapillary lancet 18. As an example, a fused silica microcapillary tube with a path length of 100 microns has a path length tolerance of ±5 μm, which reduces errors occurring in the analyte concentration analysis.

Another advantage of the lancet 18 having a square cross section is that square shape provides a two-fold increase in transverse optical interaction path length when compared to round capillaries. Thus, the square lancet 18 can be smaller than round capillaries used in a optical transmission environment, resulting in a smaller sample (e.g., as low as about 8 ηl) for filing the square lancet 18 and a smaller puncture on a test subject's skin.

Figure 3:
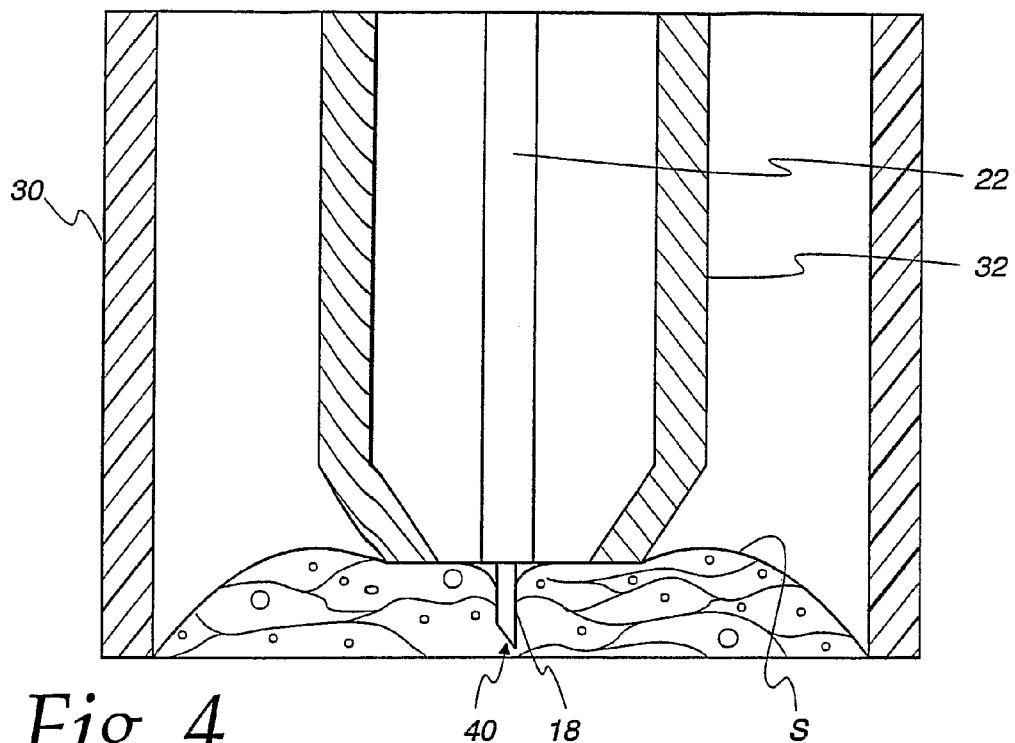
FIG. 3 is an enlarged cross-sectional view of the forward end of the lancing device of FIG. 1 shown while lancing a test subject's skin.

Referring to FIGS. 1-3, during the lancing of the test subject's skin S, the open end 36 of the outer end cap 30 is placed on an area of the test subject's skin (e.g., a forearm or finger). The plunger 14 is depressed to advance the lancet 18 from a retracted position (FIG. 2), wherein the lancet 18 is completely contained within the end caps 30, 32, to a lancing position (FIG. 3), wherein the lancet 18 extends through the open ends 36, 38 of the end caps 30, 32 and into the test subject's skin S. Movement of the plunger 14 by the user triggers a drive spring within the lancing mechanism 16 that advances the lancet 18 into a test subject's skin S. A rebound spring within the lancing mechanism 16 then retracts the tip 40 of the lancet 18 from the test subject's skin S.

According to one embodiment of the present invention, the lancing device 10 is vacuum-assisted to facilitate the production of a blood sample at the puncture site on the test subject's skin. In such an embodiment, the outer end cap 30 forms a substantially airtight seal with the forward end 34 of the device 10. The placement of the open end 36 of the outer end cap 30 against a test subject's skin S, aided by pressing against the skin, forms the substantially airtight seal. The lancing device 10 includes a vacuum member 44 such as a diaphragm or bellows that displaces air within the lancing device 10 and the end cap 30. Release of the plunger 14 by the user triggers the vacuum member 44, which evacuates air from the inner and outer end caps 32, 30.

When the vacuum member 44 is activated, the test subject's skin S is drawn inside the outer end cap 30 to the inner-locating end cap 32 as is depicted in FIG. 3. As the created vacuum pulls the test subject's skin S into the device 10, the test subject's skin S bulges around the locating end cap 32. The test subject's skin S is stretched flat across the open end 38 of the inner end cap 32. This stretched, flat skin facilitates sample formation and collection. The vacuum holds the skin and puncture sight in a fixed position while the sample harvesting occurs.

Figure 4:
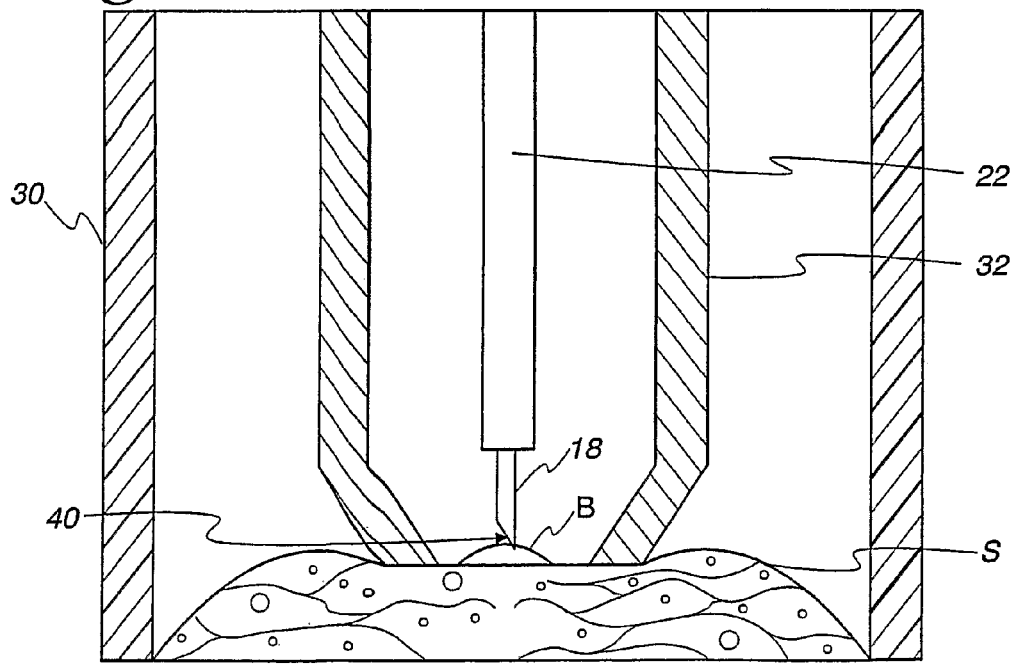
FIG. 4 is an enlarged cross-sectional view of the forward end of the lancing device of FIG. 1 shown while harvesting a body fluid sample.

Referring now to FIG. 4, after the lancet 18 punctures the test subject's skin S, a body fluid sample B (e.g., blood) forms on the skin S at the puncture site. As discussed above, the lancet 18 is hollow for harvesting the body fluid sample produced at the lance site. The lancing mechanism 16 holds the skin under vacuum and positions the hollow tip 40 of the lancet 18 in a collection position adjacent the lance site for collecting the produced body fluid sample B. The sample B contacts the hollow lancet 18 and the sample moves into the lancet 18 via capillary action. If the tip 40 of the microcapillary lancet 18 rests too far from the skin S, the sample B will not be drawn into the microcapillary channel. And if the tip 40 of the microcapillary lancet 18 rests on or below the puncture site, it may cause discomfort to the user, and a sample may not be drawn into the tip 40 of the lancet 18.

A reagent or enzymatic indicator system is disposed within the lancet 18 for reacting with the analyte of interest in the harvested sample for producing a colorimetric reaction indicative of the analyte concentration in the body fluid sample. The colorimetric reaction is read by optical instruments as it described below in connection with FIG. 5. Colorimetric testing is described in detail in U.S. Pat. No. 6,181,417 B1 (entitled "Photometric Readhead with Light Shaping Plate"); U.S. Pat. No. 5,518,689 (entitled "Diffuse Light Reflectance Readhead"); and U.S. Pat. No. 5,611,999 (entitled "Diffuse Light Reflectance Readhead"); each of which is incorporated herein by reference in its entirety.

Figure 5:
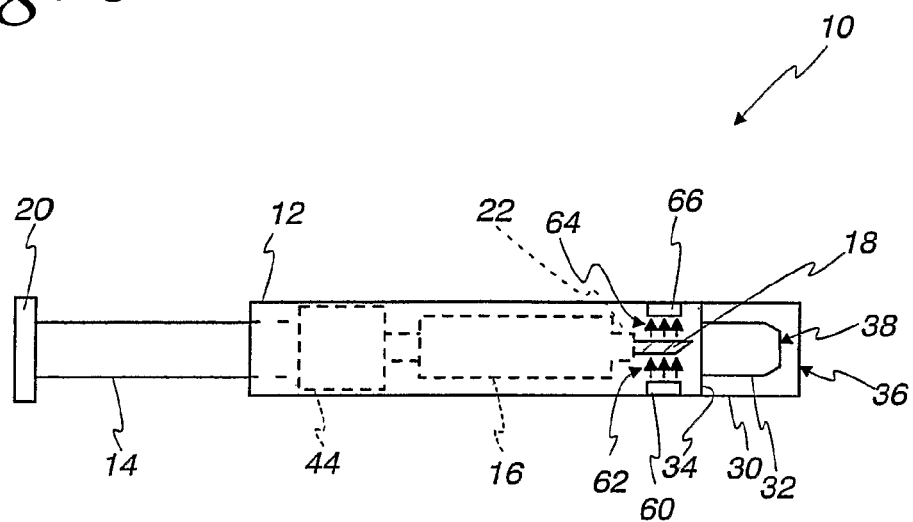
FIG. 5 is a side view of a lancing device according to an another embodiment of the present invention.

Referring now to FIG. 5, the lancing mechanism 16 retracts the lancet 18 away from the skin S (i.e., into the lancing device 10) after the sample B is collected from the lance site on the skin S for analyzing the blood according to one embodiment of the present invention. Alternatively, the lancing device 10 may maintain the lancet 18 in the collection position for analyzing the analyte concentration in the blood sample. The lancing device 10 includes an illumination unit 60, which may include a light source such as an LED, illumination optics for directing and collimating light, or both. Alternatively, the illumination unit 60 may comprise the output end of a fiber optic cable that pipes in light from a light source.

The colorimetric reaction within the substantially optically clear lancet 18 between the reagent and the analyte of interest in the harvested body fluid sample is measured using transmission spectroscopy. The illumination unit 60 outputs a monochromatic collimated beam of light 62 onto the microcapillary lancet 18. Light transmitted through the microcapillary lancet 18—referred to with reference number 64—is detected by a light detector 66 that outputs a signal indicative of the received light. The detected transmitted light is then compared to a reference sample (e.g., light from the source directly detected by the detector without the sample or lancet 18 present). The difference in light absorption between the two is used to determine the analyte concentration in the blood sample. The results of the analysis are communicated to the user via a user interface including a display (not shown) of the lancing device 10.

According to an alternative embodiment of the present invention, the amount of light transmitted through the sample is used to determine the time at which to begin analyzing the reaction between the reagent and the analyte of interest. For example, the detector 66 may constantly detect light transmitted through the lancet 18 upon retracting the lancet 18 to analyze the sample. Once the detector 66 detects that the light transmitted through the lancet 18 is consistent with a sample being contained within the lancet 18, the processor waits a predetermined about of time after the expiration of which the transmitted light detected by the detector 66 is used by the processor to determine the analyte concentration in the fluid sample. Because the colorimetric reaction requires a predetermined about of time to develop, only transmitted light detected after the expiration of the predetermined time are used in the analysis. Waiting for the reaction to develop guards against an inaccurate analysis according to one embodiment of the present invention.

Figure 6:
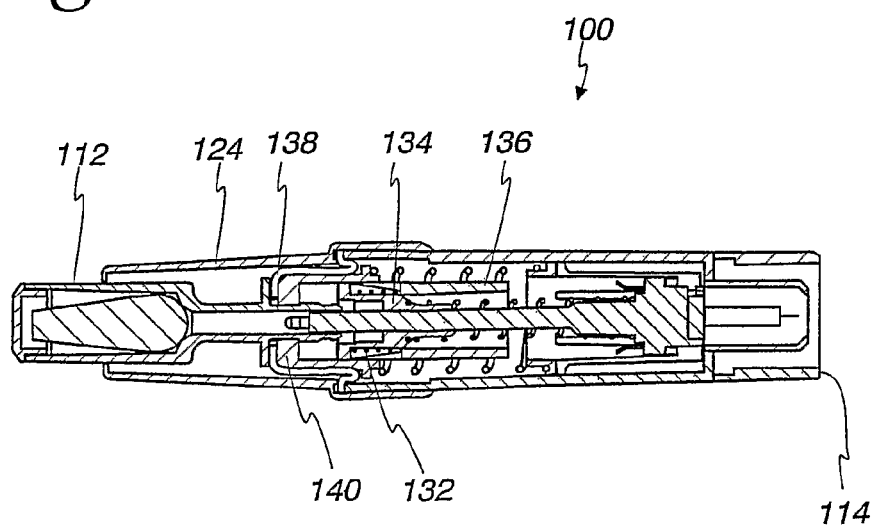
FIG. 6 is a side view of a vacuum-assisted lancing device according to another embodiment of the present invention.

Referring now to FIG. 6, a vacuum-assisted lancing device 100 is shown, which may be adapted for use as the lancing device 10 according to an alternative embodiment of the present invention. A vacuum member, such as a diaphragm 138, within the lancing device 100 is activated when the plunger 112 is depressed by the user and travels toward the open end of the lancing device 100. As the plunger 112 is depressed, a rebound spring 132 captured between a return 134 and a release 136 is expanded and extended. This action displaces the rolling diaphragm 138 toward the end cap 114. A central portion of the rolling diaphragm 138 is secured to the stem of the plunger 112 and a piston 140 such that the central portion moves with the plunger 112. The interfaces between the rolling diaphragm 138 and the stem of the plunger 112 and a housing 124 of the device 100 are air tight. The displacement of the rolling diaphragm 138 displaces air in the housing 124 creating a vacuum. Further details of the vacuum-assisted lancing device 100 illustrated in FIG. 4, which may be used in connection with alternative embodiments of the present invention, are described in U.S. Pat. No. 6,152,942, entitled "Vacuum Assisted Lancing Device," which is incorporated herein by reference in its entirety.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. An apparatus for lancing the skin of a test subject, collecting a body fluid sample from the lanced site on the skin of the test subject, the apparatus comprising:
   a body having an open end;
   a hollow lancet having a tip adapted to puncture skin and to collect a body fluid sample, the interior of the hollow lancet forming a channel for moving a fluid sample from the tip to a reaction area;
   a lancing mechanism disposed within the body, the lancing mechanism coupled to the lancet at an end of the lancet opposite the tip, the lancing mechanism being adapted to move the lancet between a retracted position, a lancing position for puncturing the skin of a test subject, and a collection position for collecting the body fluid sample;
   an outer end cap having a first end coupled to the open end of the body and a second end for contacting the skin of the test subject, the outer end cap forming a first aperture therein that the tip of the lancet enters when in the lancing position, the outer end cap having a wall extending to the second end thereof; and
   an inner end cap disposed within the outer end cap, the inner end cap having a first end coupled to the open end of the body and a second end forming a second aperture therein that the tip of the lancet enters when in the lancing position, the second end being adapted to contact the skin of the test subject when the lancet is in the collecting position, the inner end cap having a wall extending to the second end thereof, the wall of the outer end cap extending farther towards the skin than the wall of the inner end cap during lancing such that the skin of the test subject is drawn inside of the outer end cap and contacts the inner end cap,
   wherein the second end of the outer end cap and the second end of the inner end cap remain in contact with the skin in the lancing position to assist in sample formation and collection.

2. The apparatus of claim 1 wherein the lancet comprises fused silica.

3. The apparatus of claim 1 wherein the lancet has a polygonal cross-section.

4. The apparatus of claim 1 further comprising a vacuum member for evacuating air from the inner and outer end caps, the vacuum member being adapted to position the skin of the test subject against the second end of the inner end cap.

5. The apparatus of claim 4 wherein the vacuum member comprises a diaphragm.

6. The apparatus of claim 4 wherein the vacuum member comprises bellows.

7. The apparatus of claim 1 further comprising:
a light source for illuminating the reaction of the reagent and the analyte in the body fluid sample; and
a light detector for detecting light transmitted through the reaction.

8. The apparatus of claim 1 wherein the lancet has a square or rectangular cross-section.

9. The apparatus of claim 1 wherein the retracted position and the collection position are substantially the same.

10. The apparatus of claim 1 wherein the inner end cap remains entirely disposed within the outer end cap during the retracted position, the lancing position and the collection position.

11. A method for lancing the skin of a test subject and collecting a produced body fluid sample from the lanced site on the skin of the test subject for determining the concentration of an analyte in the body fluid sample with a lancing and collection device, the lancing and collection device including a substantially optically clear, hollow lancet having a tip for puncturing skin, the method comprising the acts of:
placing an outer end cap of the device against the skin of a test subject;
puncturing the skin with the lancet in a lancing position;
positioning the punctured skin against an edge of an inner end cap of the device, the inner end cap being disposed within the outer end cap, the outer end cap extending farther towards the skin than the inner end cap during lancing such that the skin of the test subject is drawn inside the outer end cap and contacts the inner end cap;
disposing the tip of the lancet a predetermined distance from the skin pulled against the edge of the inner end cap; and
collecting the body fluid sample from the puncture skin with the tip of the lancet in a collecting position;
wherein the outer end cap and the inner end cap remain in contact with the skin in the lancing position to assist in sample formation and collection.

12. The method of claim 11 wherein the hollow lancet includes a reaction area with a reagent adapted to produce a colorimetric reaction indicative of the analyte concentration in the sample, the method further comprising the acts of moving the collected body fluid sample from the tip of the lancet to the reaction area via capillary action.

13. The method of claim 11 wherein the analyte is glucose.

14. The method of claim 11 wherein the body fluid sample is blood.

15. The method of claim 12 further comprising the act of measuring a colorimetric reaction.

16. The method of claim 15 wherein the act of measuring further comprises the acts of:
illuminating the colorimetric reaction within a hollow, substantially clear lancet with a light source; and
measuring the amount of light transmitted through the colorimetric reaction with a light detector.

17. The method of claim 16 further comprising the act of measuring the amount of light transmitted through the lancet to determine the start time of the colorimetric reaction.

18. The method of claim 11 wherein the act of positioning further comprising the act of evacuating the air from the inner end cap with a vacuum member of the device.

19. The method of claim 11 further including analyzing the body fluid sample for determining the analyte concentration in the body fluid sample while the collected body fluid sample remains in the lancet.

20. The method of claim 19 wherein the capillary channel of the hollow lancet has an inlet, and the act of collecting further comprises positioning the inlet of the capillary channel adjacent the lanced skin.

21. The method of claim 19 wherein the lancing device includes an end cap, the method further comprising the act of positioning the skin against the end cap for maintaining the skin in a fixed position.

22. The method of claim 21 wherein the act of positioning further comprises the act of activating a vacuum member.

23. The method of claim 19 wherein the method further comprises the act of maintaining the skin in a fixed position while collecting the body fluid sample.

24. The method of claim 19 wherein the capillary channel contains a reagent for reacting with the analyte in the body fluid sample and producing a colorimetric reaction indicative of the concentration of the analyte in the body fluid sample.

25. The method of claim 24 wherein the act of analyzing further comprises the act of optically analyzing the body fluid sample.

26. The method of claim 25 wherein the act of optically analyzing comprises the acts of:
illuminating the colorimetric reaction within the hollow lancet with a light source; and
measuring the amount of light transmitted through the colorimetric reaction with a light detector.

27. The method of claim 26 further comprising the act of measuring the amount of light transmitted through the lancet to determine the start time of the colorimetric reaction.

28. The method of claim 19 wherein the hollow lancet is substantially optically clear.

29. The method of claim 28 wherein the hollow lancet has a polygonal cross section.

30. The method of claim 28 wherein the hollow lancet has a rectangular cross section.

31. The method of claim 28 wherein the hollow lancet has a square section cross section.

32. The method of claim 19 wherein the analyte is glucose.

33. The method of claim 19 wherein the body fluid sample is blood.

* * * * *

UNITED STATES PATENT AND TRADEMARK OFFICE
CERTIFICATE OF CORRECTION

PATENT NO.        : 8,398,567 B2
APPLICATION NO.   : 10/590531
DATED             : March 19, 2013
INVENTOR(S)       : Kuriger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 889 days.

Signed and Sealed this
Second Day of December, 2014

Michelle K. Lee
*Deputy Director of the United States Patent and Trademark Office*